US008088118B2

(12) United States Patent
Reynolds et al.

(10) Patent No.: US 8,088,118 B2
(45) Date of Patent: Jan. 3, 2012

(54) DEVICE FOR TRANSFERRING FLUID FROM A CARTRIDGE TO A CONTAINER

(75) Inventors: David L. Reynolds, Bromont (CA); Daniel MacDonald, Bromont (CA); Julie Trepanier, Sherbrooke (CA); Steven Raymond, Bromont (CA); Caroline Lavoie, Waterloo (CA)

(73) Assignee: Duoject Medical Systems Inc., Bromont, Quebec (CA)

( * ) Notice: Subject to any disclaimer, the term of this patent is extended or adjusted under 35 U.S.C. 154(b) by 579 days.

(21) Appl. No.: 12/157,867

(22) Filed: Jun. 13, 2008

(65) Prior Publication Data

US 2009/0082751 A1 Mar. 26, 2009

(51) Int. Cl.
*A61B 19/00* (2006.01)
*A61M 37/00* (2006.01)

(52) U.S. Cl. ........ 604/413; 604/411; 604/412; 604/414; 604/416; 604/86; 604/89; 604/90

(58) Field of Classification Search .................. 604/403, 604/411–416, 86–90
See application file for complete search history.

(56) References Cited

U.S. PATENT DOCUMENTS

| | | | | |
|---|---|---|---|---|
| 3,489,147 | A * | 1/1970 | Shaw | 604/88 |
| 4,861,335 | A * | 8/1989 | Reynolds | 604/88 |
| 5,330,426 | A * | 7/1994 | Kriesel et al. | 604/89 |
| 5,653,686 | A * | 8/1997 | Coulter et al. | 222/1 |
| 6,981,963 | B2 * | 1/2006 | Barker et al. | 604/90 |

* cited by examiner

*Primary Examiner* — Leslie Deak
(74) *Attorney, Agent, or Firm* — Eric Fincham

(57) ABSTRACT

A system and method for transferring a fluid from a first container to a second container, the system comprising a first container (112) having a fluid (126) therein, the first container being sealed by a septum (124) and a piston (122), the second container being sealed at its mouth by a pierceable septum (132) and having a plunger (130) at the opposite end, a moveable needle shuttle (116) having first (144) and second (146) piercing ends, the arrangement being such that upon advancement of the first container with respect to the second container, a second one of the piercing ends (144) is adapted to pierce plunger (130) of the second container and a first piercing end (146) being designed to pierce the septum (124) of the first container.

3 Claims, 15 Drawing Sheets

DEVICE FOR TRANSFERRING FLUID FROM A CARTRIDGE TO A CONTAINER

FIELD OF THE INVENTION

The present invention relates to a transfer device and more particularly, relates to a transfer device suitable for transferring fluid contents from a first cartridge to a second container.

BACKGROUND OF THE INVENTION

In the pharmaceutical field, medicants can be packaged in a first type of container and need to be transferred to a second type of container. The reason could be that the second type of container is a specialized one which is difficult to fill on known production lines. A second situation can arise when it is desired to transfer a fluid into a second container which may contain a second drug component which is to be mixed with the first fluid. In this regard, reference may be had to PCT Application CA2005/001839, the teachings of which are hereby incorporated by reference.

SUMMARY OF THE INVENTION

It is an object of the present invention to provide a system for transferring a fluid from a first container to a second container.

It is a further object of the present invention to provide a system for transferring a fluid from a first container to a second container in a sterile environment.

It is a further object of the present invention to provide a system for transferring a fluid from a first container to a second container while eliminating substantially all air or other gas in the second container.

According to one aspect of the present invention, there is provided a system for transferring a fluid, the system comprising a housing, a first container having a fluid therein, the first container having an open top, the open top being sealed by a septum, a piston located within the first container, the piston and the septum defining a compartment having the fluid, a second container, the second container having a body, a cavity within the body, an open top and an open bottom, the open top being sealed by a pierceable septum, a plunger within the cavity, the plunger being located proximate the septum so as to minimize any air between the pierceable septum and the plunger, the first container and the second container being located within the housing at opposite ends thereof, a moveable needle shuttle, the needle shuttle having first and second piercing ends and having a fluid passageway extending between the piercing ends, the arrangement being such that a first one of the piercing ends is adapted to initially pierce the plunger of the second container, and a second one of the piercing ends being designed to pierce the septum of the first container when one of the containers is moved towards the other of the containers to contact the piercing ends.

According to a further aspect of the present invention there is provided a method for transferring a fluid from a first container to a second container, the first container having an open top sealed by a septum, a piston located within the first container, the piston and the septum defining a compartment having the fluid therein, the second container having a body, a cavity within the body, an open top and an open bottom, the open top being sealed by a pierceable septum, a plunger within the cavity, the plunger being located proximate the septum so as to minimize any air between the septum and the plunger, comprising the steps of supplying a housing having a moveable shuttle therein, the shuttle having first and second piercing members located at either end thereof with a fluid passageway extending between the first and second piercing ends, placing the second container within the housing, placing said first container having the fluid therein within the housing, advancing one of the containers to cause the piercing members to pierce the plunger of the second container and the pierceable septum of the first container, exerting pressure on a first container piston to cause the fluid to pass from the first container through the fluid passageway into the second container and cause the plunger to move rearwardly towards the open bottom.

According to a still further aspect of the present invention there is provided a system for transferring a fluid, the system comprising a housing, a first container having a fluid therein, the first container having an open top, a septum sealing the open top, a second container, the second container having a body, a cavity within the body, an open top and an open bottom, the open top being sealed by a pierceable septum, and a plunger within the cavity for sealing the open bottom, a vent from within the second container to the exterior thereof, a hydrophobic membrane sealing the vent, the first and second containers being mounted at opposite ends of the housing, a moveable needle shuttle mounted in the housing intermediate the first and second containers, the needle shuttle having first and second piercing ends, a fluid passageway extending between the first and second piercing ends.

According to a still further aspect of the present invention there is provided a method for transferring fluid from a first container to a second container, the method comprising the steps of supplying a first container having a fluid therein, the first container having an open end sealed by a pierceable septum, a second container for receiving the fluid to be transferred thereto, the second container having a body, a cavity within the body, an open top and an open bottom, the open top being sealed by a pierceable septum, a plunger sealing the open bottom, a vent extending from the cavity to the exterior of the container, a hydrophobic membrane mounted in the vent, a needle shuttle having first and second piercing ends with a fluid passageway extending between the first and second piercing ends, placing the first container within the housing at one end thereof, placing the second container in the housing at a second end thereof, advancing the first container so as to cause the needle shuttle to advance towards the second container and thereby cause the second piercing end to pierce the plunger of the second container, and cause the first piercing end to pierce the septum of the first container, and exerting a pressure on the piston to cause the fluid to be advanced to the second container and to expel substantially all the air therefrom through the vent and the hydrophobic membrane.

According to a still further aspect of the present invention there is provided a system for transferring a fluid, the system comprising, a housing, a first container having a fluid therein, the first container having an open top and an open bottom, the open top being sealed by a septum and the open bottom being sealed by a piston, a second container, the second container having a body, a cavity within the body, an open top and an open bottom, the open top being sealed by a pierceable septum, a plunger within the cavity sealing the open bottom, the first container and the second container being located within the housing at opposite ends thereof, a moveable needle shuttle, the needle shuttle having first and second piercing ends and having a fluid passageway extending between the piercing ends, a pusher mechanism located rearwardly of the first container, the pusher mechanism having a first pushing element and a second pushing element, the first pushing element being designed to push the body of the first container, the second pushing element being designed to push the piston, the arrangement being such that upon an initial pushing movement, the first pushing element contacts the body to advance the first container and means to then permit the second pusher element to exert pressure on the piston.

According to a still further aspect of the present invention there is provided a system for transferring a fluid from a first container to a second container, the system comprising an upper housing, the upper housing having an open top and an open bottom, the open top being designed to receive the second container, the second container having a body, a cavity within the body, an open top and an open bottom, the open top of the second container being sealed by a pierceable septum, a plunger within the cavity, the plunger being located proximate the septum so as to minimize any air between the septum and the plunger, a vent extending between the cavity and exterior of the body, a hydrophobic membrane sealing the vent, a lower housing, the lower housing having an open top and an open bottom, the open bottom being designed to receive said first container, a needle hub mounted intermediate the first and second containers, the needle hub having a cannula with first and second piercing ends, a fluid passageway extending between the first and second ends, a sheath extending about the first piercing end, the sheath being attached to the needle hub, and sealing means extending between an outer wall of the needle hub and an adjacent wall.

As used herein, the terms piston, plunger and septum all refer to a member which is pierceable by a needle or other piercing member. Generally, the term septum will denote a member about the mouth of the container while a piston or a plunger will refer to a member which is moveable within the body of the container.

Also, as used herein, the term distal will generally refer to that end of an element or member which is at a dispensing end while the term proximal will refer to that end from which the fluid is being moved.

In one embodiment of the invention, the fluid is to be transferred from a first container which is a standard pharmaceutical container such as a cartridge which is designed to be filled on conventional filling lines. The second container will generally be one which is not fillable or difficult to fill on a standard pharmaceutical filling line. However, as previously mentioned, the system and method of the present invention could also be used to transfer a fluid into a second container which may contain a second drug component which is to be mixed with the first fluid.

In a first embodiment of the invention, the second container is supplied to the transfer device with the plunger thereof being located proximate the septum covering the mouth of the container. The container is then filled through the plunger and thus the amount of air in the container is minimized. The first container may typically be a syringe body and the shuttle or needle hub carries a cannula having two separate piercing ends, one designed to pierce the septum of the first container and the second designed to pierce the plunger of the second container.

The order of the piercing may vary. Thus, one may utilize an arrangement wherein a force exerted on the body of the first container will cause the needle hub or shuttle to advance such that the second piercing end will pierce the plunger of the second container followed sequentially by piercing of the septum of the first container. Alternatively, using special means so as not to pressurize the fluid in the first container, the septum of the first container may be initially pierced followed by piercing of the plunger of the second container.

In one of the embodiments of the present invention, various sealing means are employed in order to maintain sterility during the transfer operation.

BRIEF DESCRIPTION OF THE DRAWINGS

Having thus generally described the invention, reference will be made to the accompanying drawings illustrating embodiments thereof, in which.

DETAILED DESCRIPTION OF THE INVENTION

Figure 1:
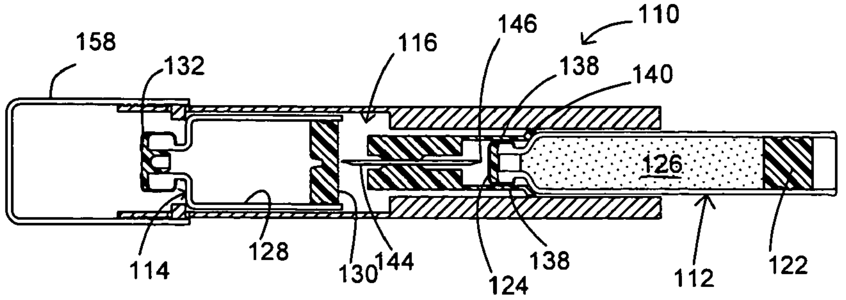
FIGS. 1 to 5 are side sectional views of a first embodiment illustrating operation of a transfer device for transferring fluid contents from a first cartridge to a second container.

Referring to the drawings in greater detail and by reference characters thereto, there is illustrated in FIG. 1 a transfer device generally designated by reference numeral 110.

Transfer device 110 includes a conventional fluid containing cartridge 112, a container 114 to which the fluid is to be transferred to, and a shuttle 116.

Cartridge 112 has a cylindrical body 120 and may have any suitable dimensions. In the illustrated embodiment, it is of an elongated configuration with a piston 122 being located at one end thereof. At the other end, there is provided a pierceable septum 124 while the cylindrical body 120 contains a fluid 126 which is to be transferred to container 114.

Container 114 has an outer wall 128 which defines a cylindrical container configuration with a pierceable plunger 130 being located at one end thereof. A pierceable septum 132 is located at the other end.

Shuttle 116 includes a main body portion 136 with legs 138 extending from one end thereof. In the illustrated embodiment, there are provided two such legs 138. Each leg 138 has at the end thereof a flange 140 which extends diagonally outwardly.

Extending through main body portion 136 is a cannula which has a first piercing tip 144 located at one end thereof and a second piercing tip 146 located at the other end. If desired, sheaths may be placed about one or both of the exposed ends of the piercing tips.

Transfer device 110 also includes an outer housing 150. On the interior wall of housing 150 there is provided a shoulder 152 wherein the wall becomes of a diminished thickness. At the end having a diminished thickness, there are provided moveable biasing elements 154. Housing 150 also includes a threaded portion 156 designed to receive a cap 158.

Figure 2A:
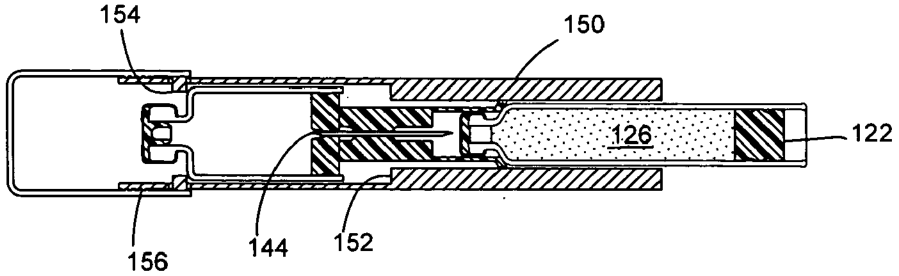

As shown in FIG. 1, cartridge 112 is loaded into transfer device 110. Subsequently, and as illustrated in FIG. 2A, continued movement of cartridge 112 will cause movement of shuttle 116 due to the engagement of legs 138 on the shoulder of the cartridge 112. This in turn will lead to the piercing of plunger 130 by pierceable tip 144 of the cannula.

Figure 2B:
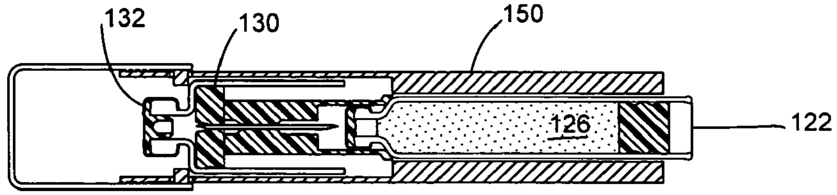
Figure 2C:
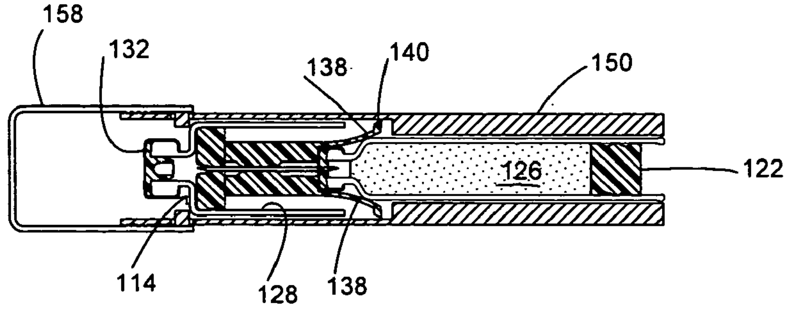

As may be seen in FIG. 2B, continued movement of the shuttle will cause plunger 130 to advance and empty container 114 of air or other gaseous material therein. Still further movement of cartridge 112 will then cause pierceable tip 146 of the cannula to pierce septum 124 of cartridge 112. It is to be noted that container 114 is not able to move due to engagement of biasing elements 154 with the shoulder thereof. As seen in FIG. 2C, the piercing of septum 124 of cartridge 112 is achieved by legs 138 passing from the thicker part of housing 150 past shoulder 152 to thereby permit the movement of cartridge 112.

Figure 3:
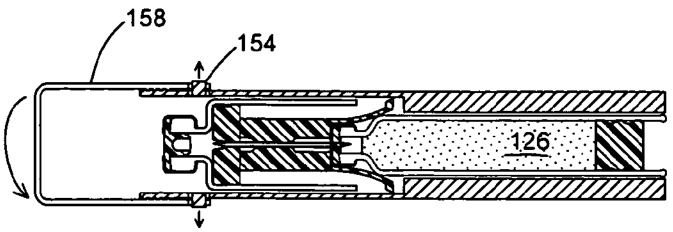

As illustrated in FIG. 3, cap 158 is then indexed and elements 154 move outwardly to engage cap 158 and to permit advancement of container 114. Moveable elements 154, in other words, are retained by cap 158 and as soon as the cap is indexed or moved upwardly, they are biased outwardly. Any suitable arrangement such as a flexible tab may be utilized.

Figure 4A:
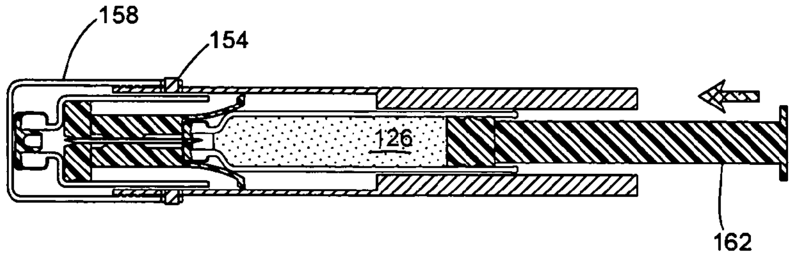
Figure 4B:
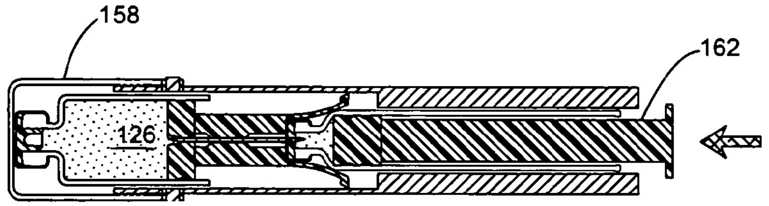
Figure 5:
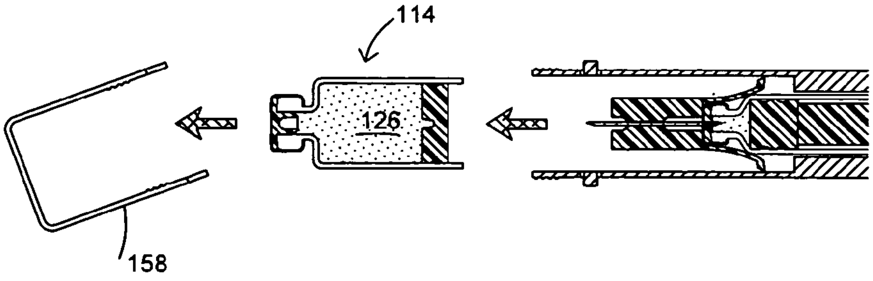
Figure 6:
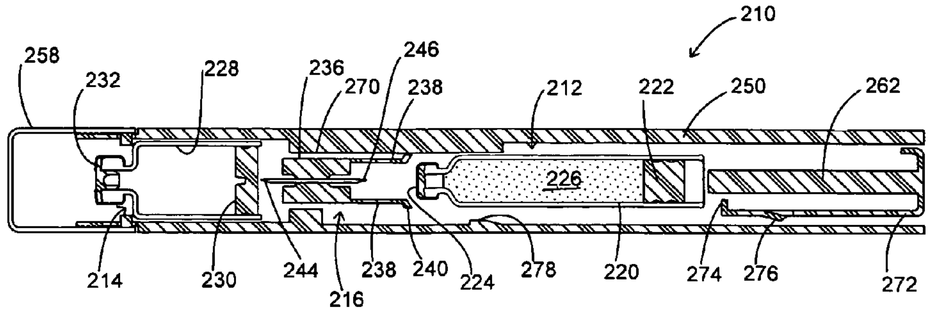
FIGS. 6 to 10 are side sectional views illustrating a further embodiment of a transfer device according to the present invention.

A piston rod 162 is then engaged against piston 122 as shown in FIGS. 4A and 4B and pressure exerted as indicated by the arrow. In so doing, fluid 126 is transferred from cartridge 112 to container 114 as illustrated in FIGS. 4A and 4B. As a final step, cap 158 is removed and access may be then had to container 114.

Reference will now be had to the embodiment illustrated in FIGS. 6 to 10. Similar reference numerals in the 200's are employed for components which are similar to those previously described.

The transfer device of this embodiment is generally designated by reference 210. Transfer device 210 includes a conventional fluid containing cartridge 212, a container 214 to which the fluid is to be transferred to, and a shuttle 216.

Cartridge 212 includes a cylindrical body 220 and has a piston 222 located at one end thereof. At the other end, there is provided a pierceable septum 224. The fluid 226 therein is contained in the cavity defined by piston 222 and septum 224.

Container 214 has an outer wall 228 which defines a generally cylindrical container and which container includes a pierceable plunger 230 at one end thereof. A septum 232 is located at the other end.

Shuttle 216 has a main body portion 236 with legs 238 extending from one end thereof. Legs 238 each have a flange 240 extending diagonally outwardly.

Shuttle 216 has a main body portion 236 through which a cannula extends. The cannula has a first piercing tip 244 located at one end thereof and a second piercing tip 246 located at the other end.

Transfer device 210 includes an outer housing 250. On the interior wall of housing 250, there is provided a first enlarged portion 266 and a second enlarged portion 268. There is also provided a somewhat smaller inwardly extending protrusion 278 as may be seen in FIG. 6.

A piston rod 262 has a leg 272 associated therewith. Leg 272 includes an inwardly extending flange 274 for reasons which will become apparent hereinbelow. Leg 272 also includes an outwardly extending protrusion 276.

Figure 7A:
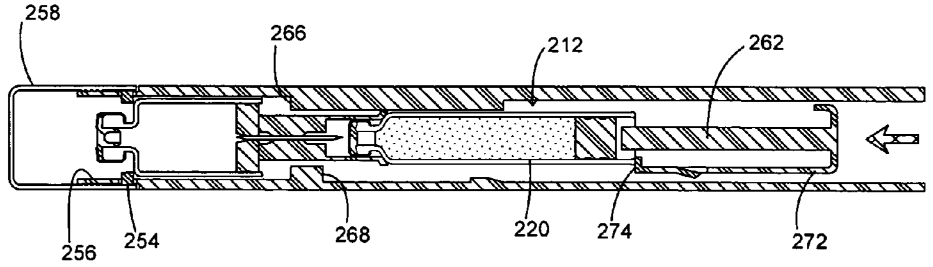
Figure 7B:
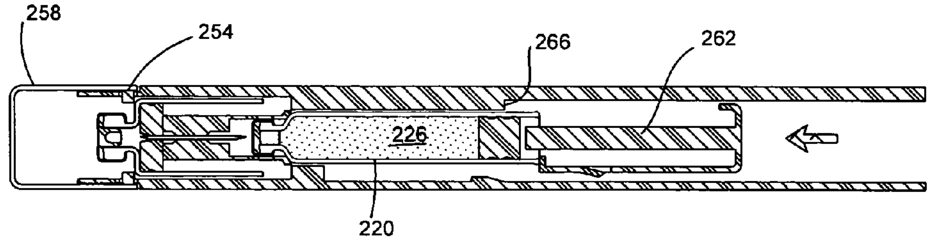
Figure 7C:
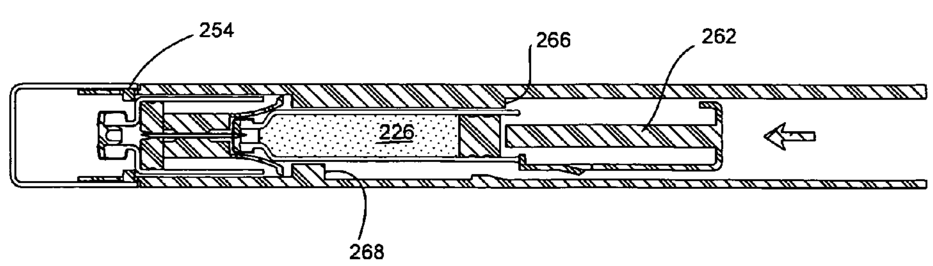

In operation, and as shown in the drawings, cartridge 212 is placed within transfer device 210 and advanced such that the shoulders of cartridge 212 engage flanges 240 of legs 238. Subsequently, as shown in FIG. 7A, piston rod 262 is advanced such that flange 274 of leg 272 will engage the bottom end of cylindrical body 220. As may be seen in FIG. 7B, continued advancement of cylindrical body 220 will cause piercing tip 244 to pierce plunger 230. Moveable elements 254 retain the shoulder of container 114 to prevent advancement thereof. As shown in FIG. 7B, the air from container 214 is removed when plunger 230 is advanced to a point proximate septum 232. Again, continued advancement of cartridge 212 is permitted, as shown in FIG. 7C, by outward movement of leg 238 as the assembly passes enlarged portions 266 and 268.

Figure 8:
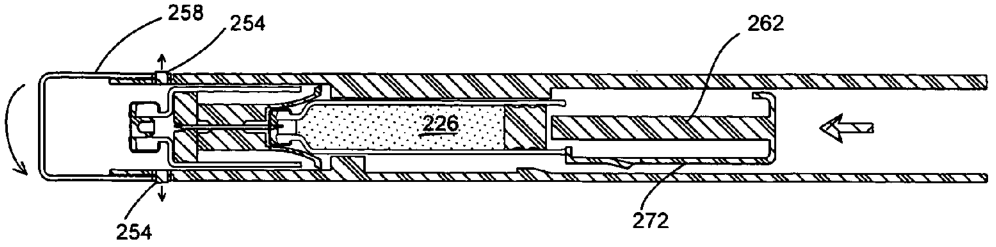
Figure 9A:
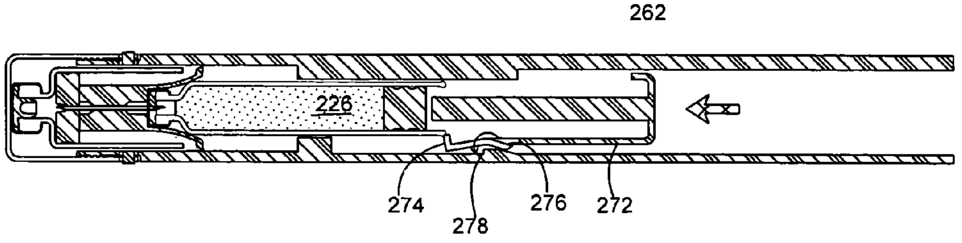
Figure 9B:
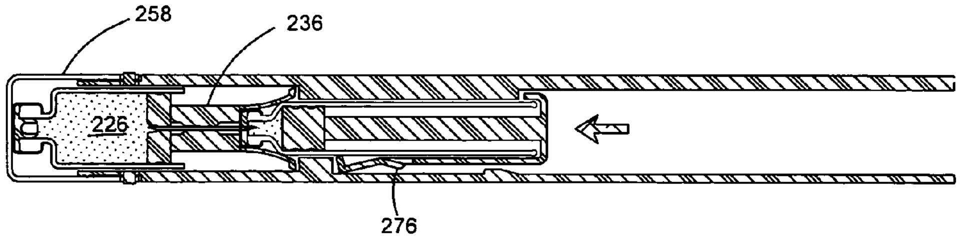
Figure 10:
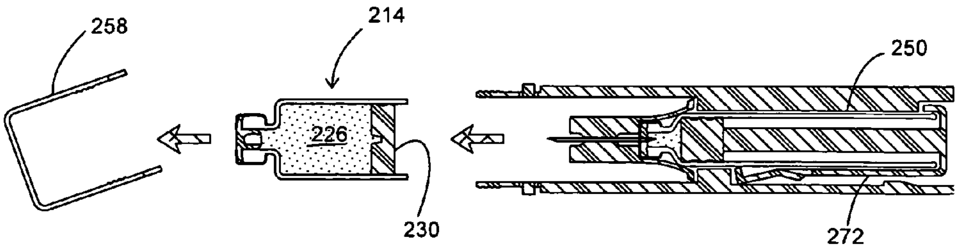
Figure 11:
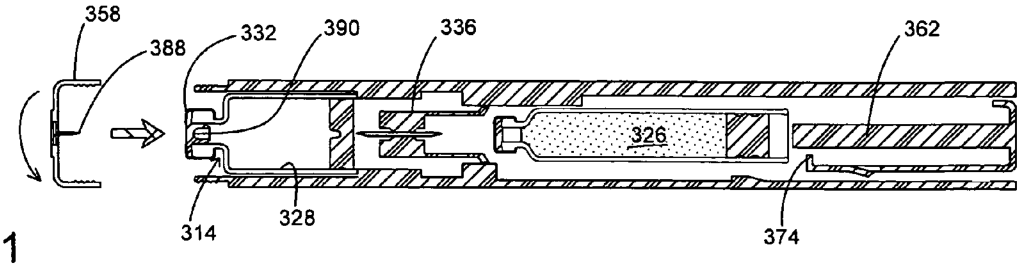
FIGS. 11 to 14 are side sectional views illustrating a third embodiment of a transfer device according to the present invention.

Subsequently, as shown in FIG. 8, cap 258 is indexed and moveable elements 254 extend are biased outwardly.

Continued pressure on plunger 262 will permit protrusions 276 and 278 to engage each other which results in the outer flexing of leg 272 and in particular flange 274. This permits piston rod 262 to act directly on piston 222 to cause the liquid 226 to pass from cartridge 212 to container 214. Subsequently, cover 258 is removed and access is had to container 214.

Reference will now be had to the embodiment of FIGS. 11 to 14 and wherein references numerals in the 300's are employed for similar components.

As this embodiment is very similar to that of FIGS. 6 to 10, only the differences will be described. In this embodiment, cover 358 has a piercing member 388 on the interior thereof. As cover 358 is placed in position, piercing member 388 will pierce the septum 332 of container 314.

A hydrophobic filter 390 covers the venting passage formed within piercing member 388 and will only permit air to escape and not any liquid. This permits the filling of container 314 to the maximum extent as all air is expelled therefrom when the liquid is transferred into the container.

Figure 12A:
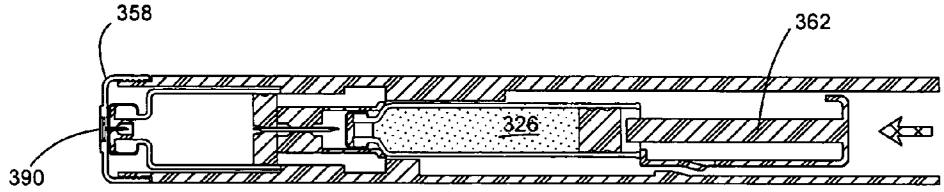
Figure 12B:
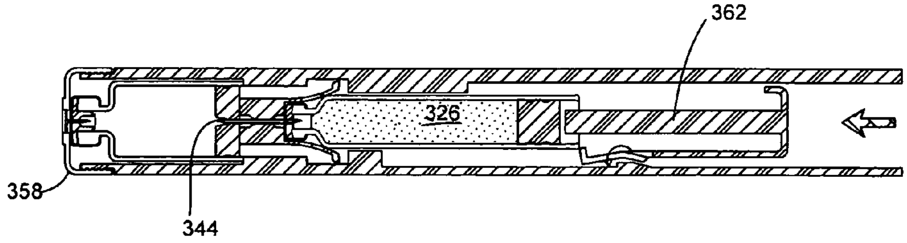
Figure 13:
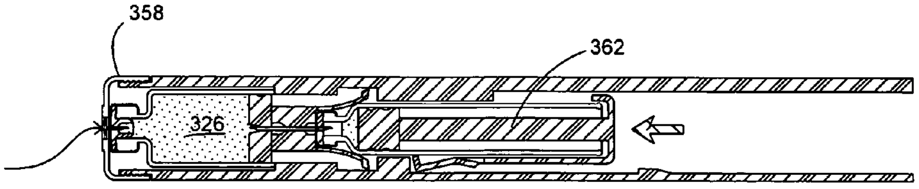
Figure 14:
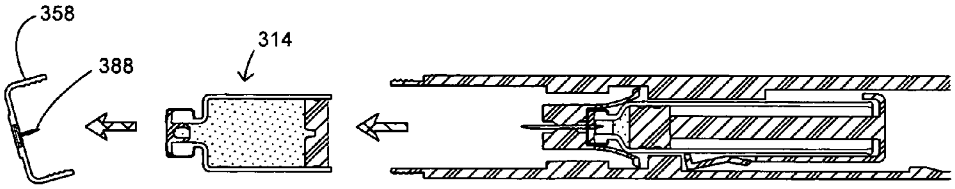

As may be seen in FIGS. 12 to 14, the same process is followed as was described with respect to FIGS. 6 to 10.

Reference will now be had to the embodiment of FIG. 15 wherein a first arrangement for maintaining sterility in the system is taught. In this embodiment, there is provided a transfer device generally by reference numeral 410 and wherein a fluid is to be transferred from a cartridge 412 to a container 414. A shuttle 416 provides fluid communication between cartridge 412 and container 414.

Cartridge 412, which contains the fluid to be transferred, has a generally cylindrical body 420 with a piston 422 located at the proximal end thereof. At its distal end, a pierceable septum 424 is provided; septum 424 and plunger 422 sealing fluid 426 therebetween.

Container 414 has an outer wall 428 with a pierceable plunger 430 being located therein adjacent the distal end of container 414. A pierceable septum 432 is located at the distal end of container 414.

Extending about the distal end of container 414 is a cap 434. As may be seen, a piercing member 435 extends through septum 432; piercing member 435 has a fluid passageway or vent 436 extending therethrough. A hydrophobic membrane 438 seats on the end of piercing member 435 to thereby cover fluid passageway 436.

Shuttle 416 includes a cannula 440 having a first piercing tip 442 and a second piercing tip 444. A sheath 425 extends about first piercing tip 442.

The transfer device includes a first outer housing 448 having an outer wall designed by reference numeral 450 and a portion of an inner wall 452. A portion of outer wall 450 and inner wall 452 extend in a parallel but spaced relationship and are joined by wall segment 451. At the distal end of inner wall 452, there is provided a small flange 454.

Outer wall 450 includes a distal wall segment 456 and an intermediate wall segment joined by a jog 458. Similarly, a jog 461 is formed at the point of joinder of intermediate wall segment 460 and a proximal end wall segment 462.

A lower housing 464 extends about cartridge 412 and has, at its distal end, a recess 466 for reasons which will become apparent hereinbelow.

A coil spring 443 extends between wall segment 451 of outer housing 448 and shuttle 416.

As shown in the drawings, a first O ring 472 extends around an outer portion of the distal end 470 of shuttle 416 to provide a sealing rolling engagement between shuttle distal end 470 and inner wall 452 of outer housing 448. A second O ring 474 provides a sealing rolling engagement between a distal end of intermediate portion 460 of outer housing and the container 414.

As will be noted, lower housing 464 has a recess 466 which engages a protrusion 467. A pusher mechanism generally designated by reference 480 includes a plunger rod 482 and an outer housing 484. Outer housing 484 has first and second protrusions 486 and 488 thereon. An outer housing 490 surrounds pusher assembly 480.

In operation, and as is shown in FIGS. 15B to 15G, pushing mechanism 480 is advanced as indicated by arrow 491. Any suitable means for applying the force may be used. In so doing, outer housing 484 and protrusion 486 engage the bottom of cartridge 412 to advance the same. As may be seen in FIG. 15C, piercing tip 442 will pass through sheath 425 and septum 424 to thereby enter cartridge 412. It will be noted that, at this point in time, liquid will not necessarily pass through cannula 440 since it is not under any pressure.

Figure 15A:
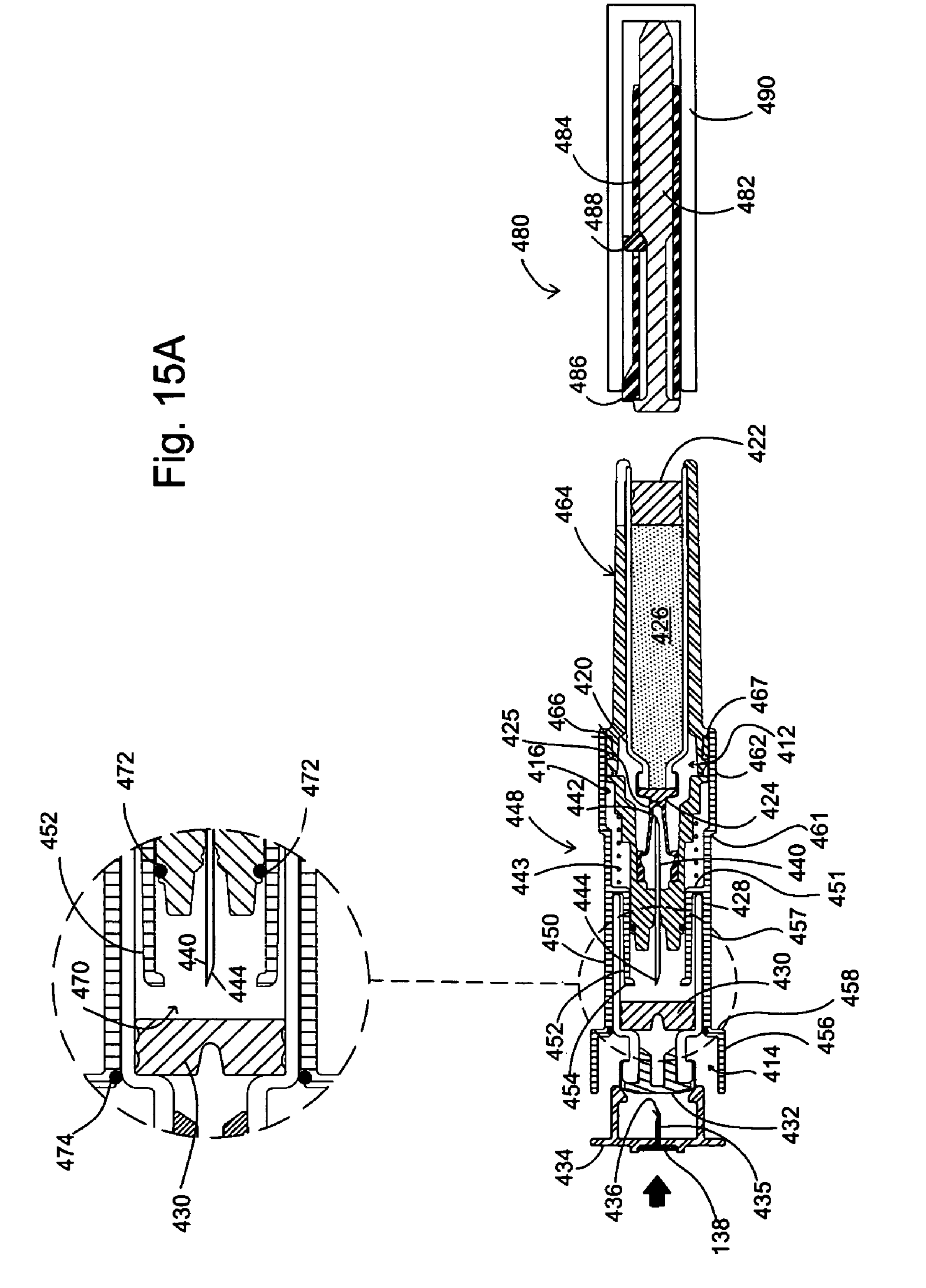
FIGS. 15A to 15G are side sectional views of a further embodiment of the present invention providing sealing means to prevent contamination and enhance sterility.
Figures 15B, 15C:
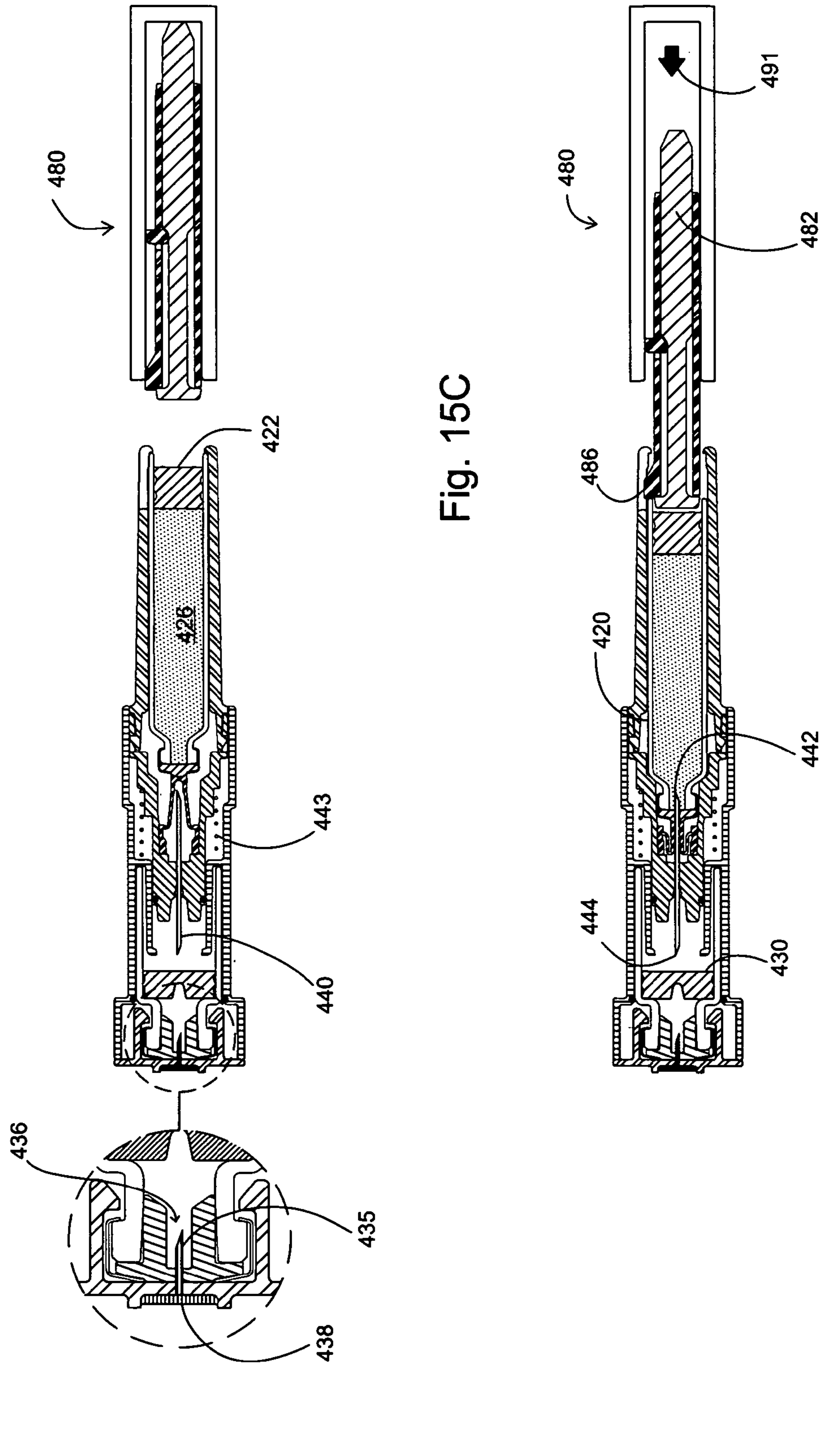
Figure 15D:
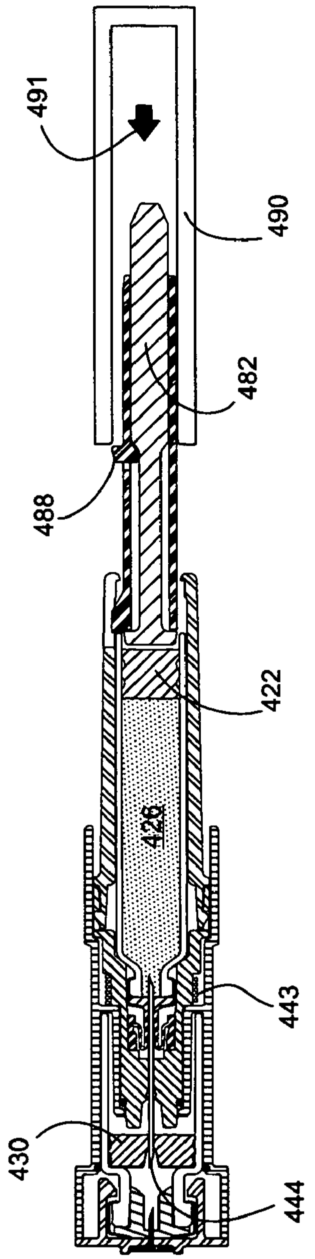
Figure 15E:
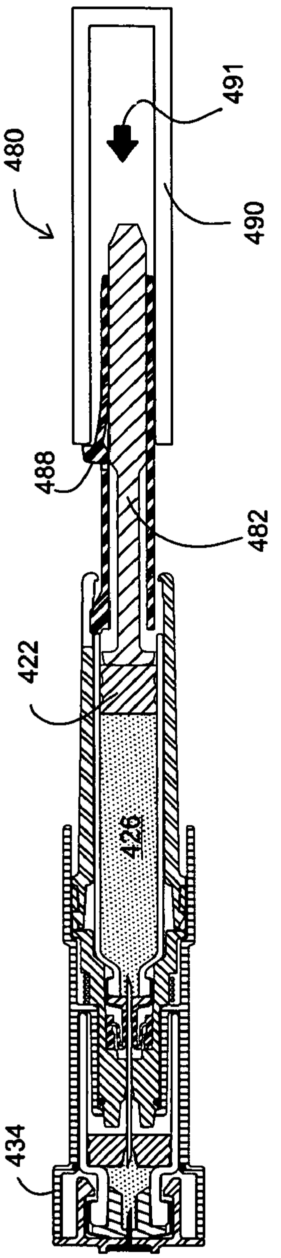
Figure 15F:
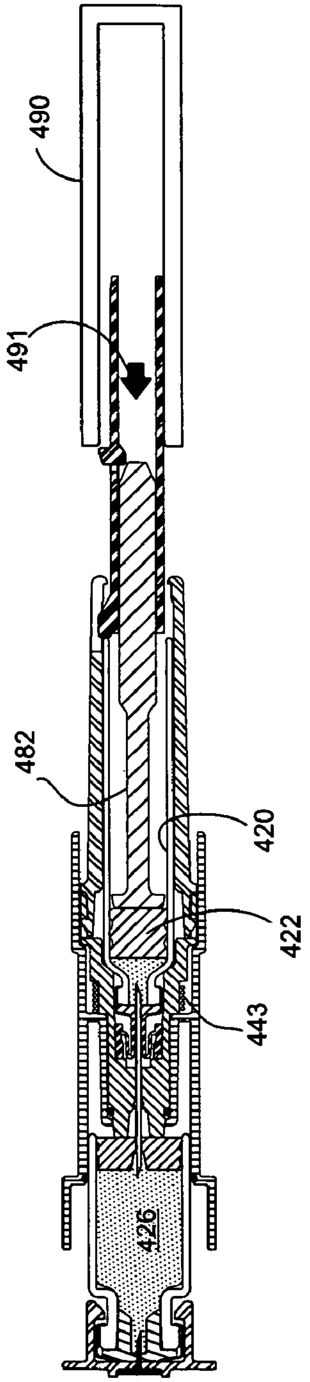
Figure 15G:
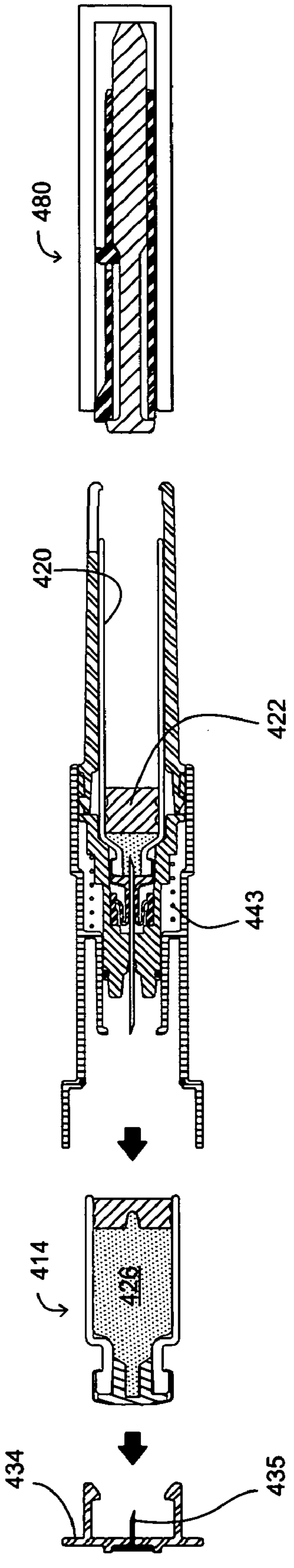

A further advancement, as shown in FIG. 15D, will compress spring 443 and needle or piercing tip 444 of cannula 440 will then pierce plunger 430. At this point in time, and as shown in FIG. 15D, plunger 482 will engage with piston 422. This is permitted when protrusion 488 passes the end of housing 490 and is thus allowed to extend outwardly and thereby release plunger rod 482. Thus, the liquid will commence passing through cannula 440 to enter the interior of container 414.

After substantially all of the liquid has been transferred, cap 434 is removed and container 414 may then be removed from the upper housing 448.

Figure 16:
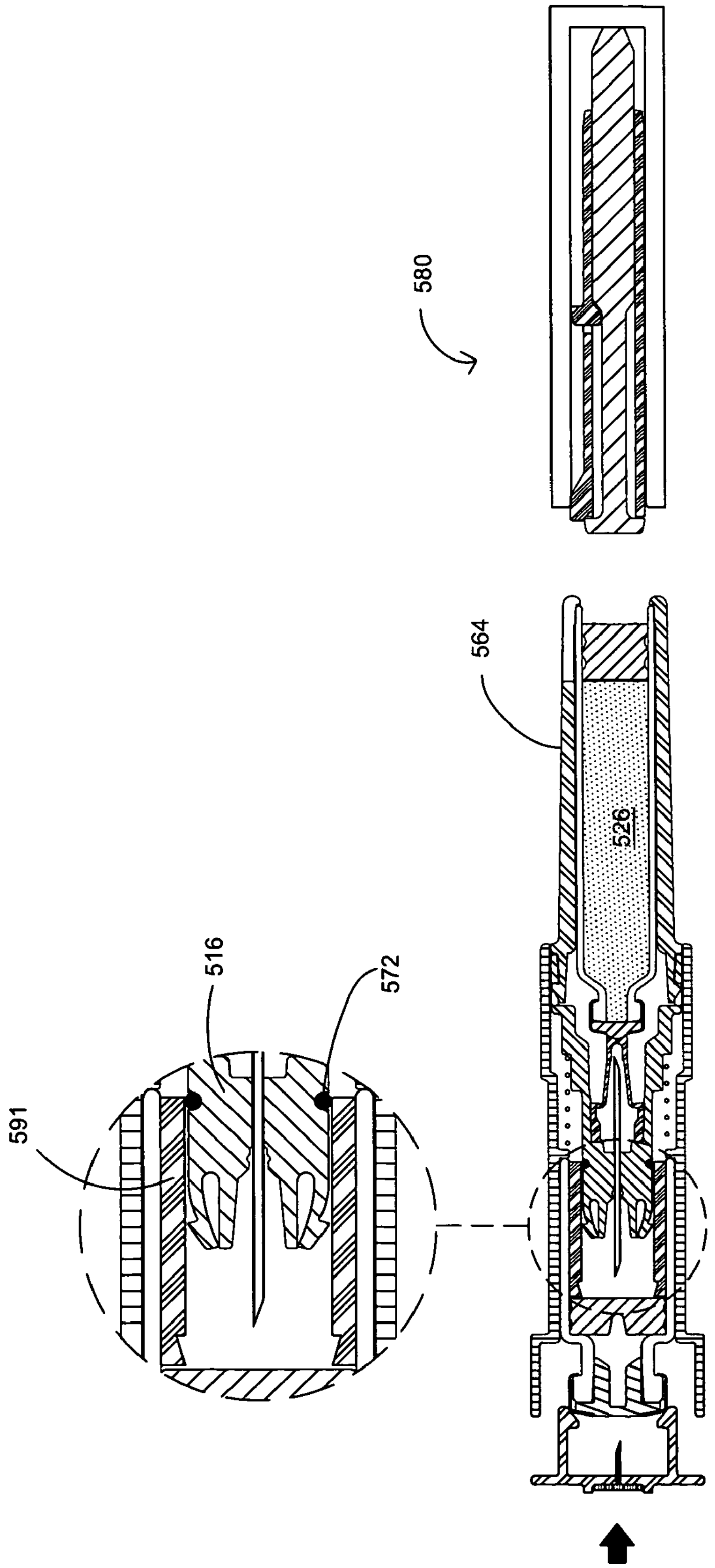
FIG. 16 is a side sectional view of a further arrangement for enhancing sterility.

FIGS. 16 to 20 illustrate various means of maintaining sterility during the transfer operation. In the embodiment of FIG. 16, O ring 572 extends around the distal end of shuttle 516. It will be noted that there is a cylinder 591 located between the outer wall 528 of container 514.

Figure 17:
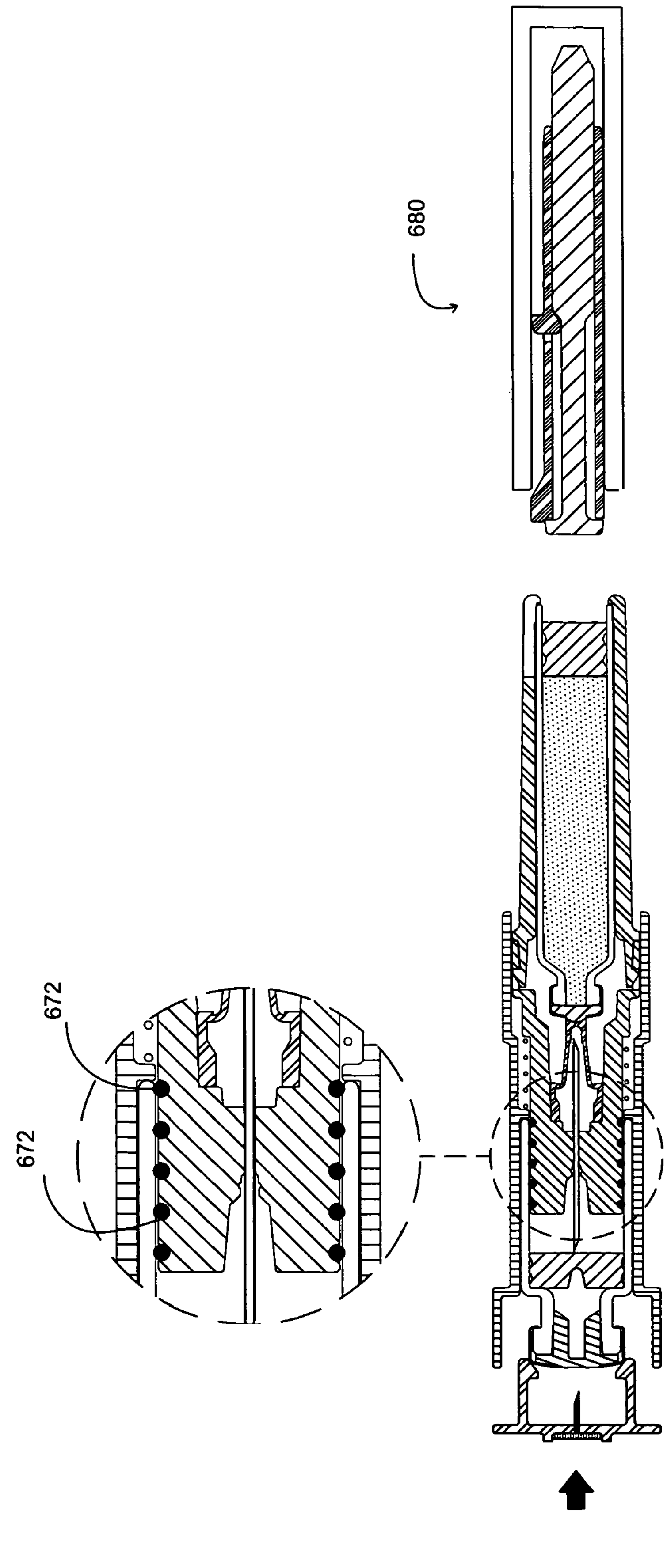
FIG. 17 is a side sectional view illustrating an embodiment using a plurality of sealing means.

In the embodiment of FIG. 17, a plurality of O rings 672 are placed about the distal end of shuttle 616.

Figure 18:
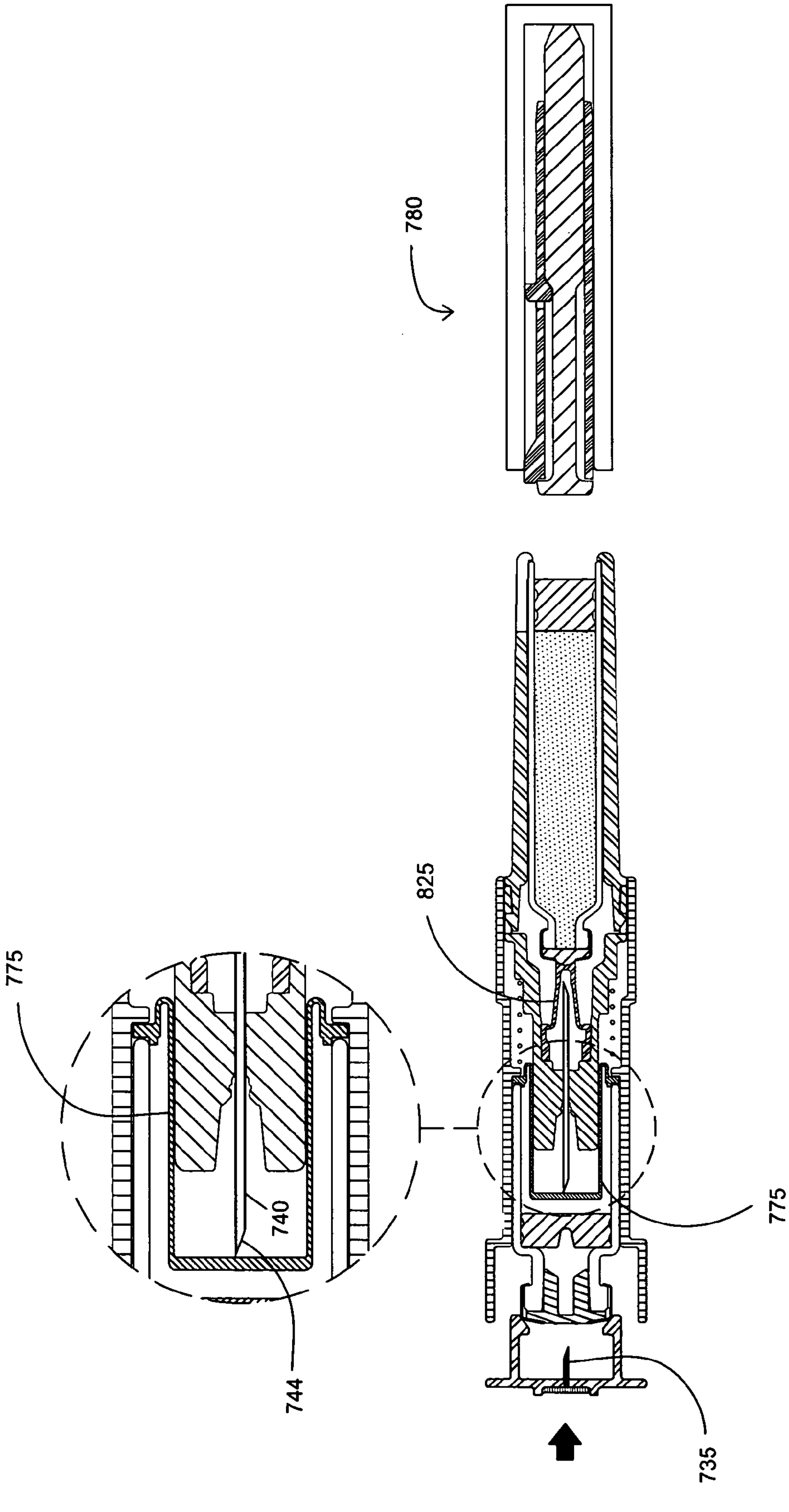
FIGS. 18 to 20 are side sectional views of further embodiments of a device having sealing means associated therewith.

FIG. 18 illustrates an embodiment wherein a collapsible sheath 775 is placed about piercing tip 444 of cannula 440. The sheath is attached to the side wall segment 757 of housing 748.

Figure 19:
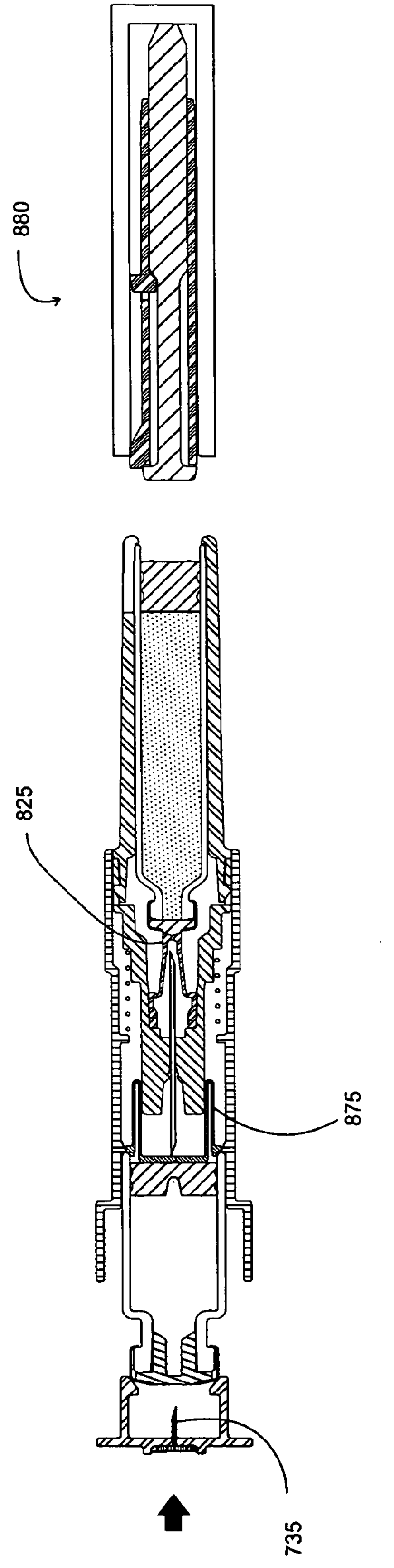

A similar arrangement is illustrated in FIG. 19 with the use of a sheath 875 which is a different place on side wall 857.

Figure 20:
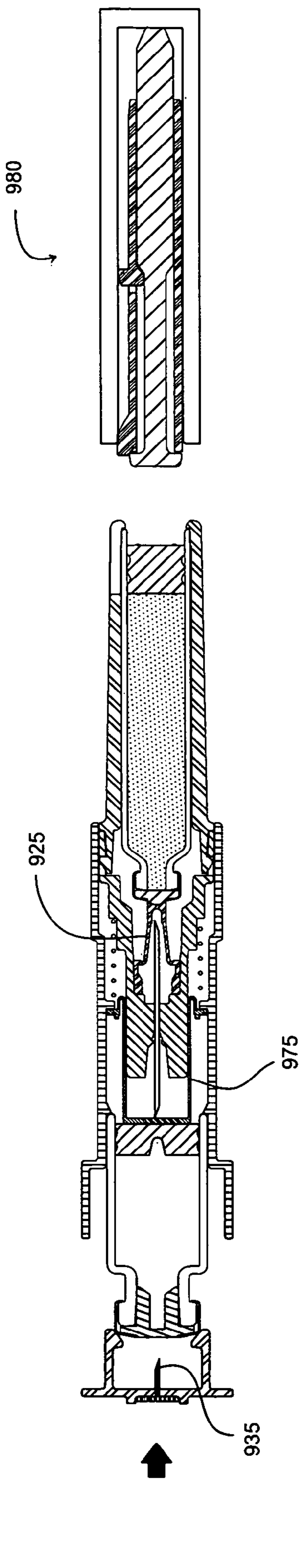

FIG. 20 illustrates a different embodiment or attachment of sheath 975 which extends about piercing tip 944 of cannula 940. In both the embodiments of FIGS. 19 and 20, it will be noted that plungers 830 and 930 respectively are located at the rear end of container 814 and 914 when initially inserted into place.

The functioning of the pusher mechanisms in FIGS. 16 to 20 is substantially equivalent to that previously described and hence will not be discussed in any greater detail.

We claim:

1. A method for transferring a fluid from a first container (412) to a second container (414), said first container having an open top sealed by a septum (424), a piston (422) located within said first container (412), said piston (422) and said septum (424) defining a compartment having said fluid (426) therein, said second container (414) having a body, a cavity within said body, an open top and an open bottom, said open top being sealed by a pierceable septum (432), a plunger (430) within said cavity, said plunger (430) being located proximate said septum (432) so as to minimize any air between said septum and said plunger, comprising the steps of:

supplying a housing (448) having a moveable shuttle (416) therein, said shuttle having first and second piercing members (442, 444) located at either end thereof with a fluid passageway extending between said first and second piercing ends;

placing said second container (414) within said housing;

placing said first container (412) having said fluid (426) therein within said housing;

advancing one of said containers (412, 414) to cause said piercing members to pierce said plunger (430) of said second container and said pierceable septum (424) of said first container;

exerting pressure on a first container piston (422) to cause said fluid (426) to pass from said first container through said fluid passageway (440) into said second container and cause said plunger (430) to move rearwardly towards said open bottom.

2. The method of claim 1 wherein the step of advancing one of said containers comprises the step of advancing said first container (112) to cause said second piercing end (144) to sequentially pierce said plunger (130) of said second container and subsequently said first piercing end (146) to pierce said pierceable septum (124) of said first container.

3. The method of claim 1 wherein the step of advancing one of said containers comprises the step of advancing said first container (412) to cause said first piercing end (442) to pierce said pierceable septum (424) of said first container, and subsequently cause said second piercing end (444) to pierce said plunger (430) of said second container.

* * * * *

UNITED STATES PATENT AND TRADEMARK OFFICE

CERTIFICATE OF CORRECTION

PATENT NO. : 8,088,118 B2
APPLICATION NO. : 12/157867
DATED : January 3, 2012
INVENTOR(S) : David L. Reynolds et al.

It is certified that error appears in the above-identified patent and that said Letters Patent is hereby corrected as shown below:

Title page, Item [22] should read

Priority date: June 13, 2007

Signed and Sealed this
Seventeenth Day of April, 2012

David J. Kappos

*Director of the United States Patent and Trademark Office*